United States Patent
Harttig

(10) Patent No.: US 8,071,048 B2
(45) Date of Patent: *Dec. 6, 2011

(54) TEST ELEMENT WITH NANOFIBERS

(75) Inventor: Herbert Harttig, Neustadt (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/158,116

(22) Filed: Jun. 10, 2011

(65) Prior Publication Data

US 2011/0263456 A1   Oct. 27, 2011

Related U.S. Application Data

(60) Continuation of application No. 12/880,441, filed on Sep. 13, 2010, which is a division of application No. 11/759,268, filed on Jun. 7, 2007, now Pat. No. 7,815,855, which is a continuation of application No. PCT/EP2005/013066, filed on Dec. 6, 2005.

(30) Foreign Application Priority Data

Dec. 7, 2004 (DE) .......................... 10 2004 058 924

(51) Int. Cl.
G01N 21/75 (2006.01)
(52) U.S. Cl. ........ 422/420; 422/421; 422/422; 422/423; 422/424; 422/425; 422/426; 422/427; 422/428; 422/429; 422/534; 422/535; 436/164; 436/169; 436/170; 435/287.1; 435/287.2; 435/287.3; 435/287.4; 435/287.5; 435/287.6; 435/287.7; 435/287.8; 435/287.9
(58) Field of Classification Search .................. 422/420, 422/421, 422, 423, 424, 425, 426, 427, 428, 422/429, 534, 535; 436/164, 169, 170; 435/287.1, 435/287.2, 287.3, 287.4, 287.5, 287.6, 287.7, 435/287.8, 287.9
See application file for complete search history.

(56) References Cited

U.S. PATENT DOCUMENTS

| | | | |
|---|---|---|---|
| 1,975,504 A | 10/1934 | Formhals | |
| 2,160,962 A | 6/1939 | Formhals | |
| 2,187,306 A | 1/1940 | Formhals | |
| 5,292,814 A | 3/1994 | Bayer et al. | |
| 2002/0106496 A1 | 8/2002 | Moxon et al. | |
| 2003/0134433 A1 | 7/2003 | Gabriel et al. | |
| 2003/0171053 A1 | 9/2003 | Sanders | |
| 2003/0217928 A1 | 11/2003 | Lin et al. | |
| 2006/0057350 A1 | 3/2006 | Ochi et al. | |

FOREIGN PATENT DOCUMENTS

| | | |
|---|---|---|
| EP | 1 564 315 A1 | 8/2005 |
| JP | A-2000-065834 | 3/2000 |
| WO | WO 02/40242 A1 | 5/2002 |
| WO | WO 03/026532 A2 | 4/2003 |
| WO | WO 03/086234 A2 | 10/2003 |
| WO | WO 03/087443 A1 | 10/2003 |
| WO | WO 2004/038073 A1 | 5/2004 |
| WO | WO 2004/099068 A2 | 11/2004 |

OTHER PUBLICATIONS

Feng, L., et al., "Super-Hydrophobic Surface of Aligned Polyacrylonitrile Nanofibers," Angew. Chem. Int. Ed. 2002, 41, No. 7, Wiley-VCH Verlag GmbH, Weinheim, Germany.

Feng, L., et al., "Creation of a super;hydrophobic Surface from an Amphiphilic Polymer," Angew. Chem. Int. Ed. 2003, 42, No. 7, Wiley-VCH Verlag GmbH & Co., Weinheim, Germany.

Fong, H., Chun, I., Reneker, D.H., "Beaded nanofibers formed during electrospinning," Polymer 40 (1999) p. 4585-4592.

Huang, Z-, Zhang, Y-Z, Kotaki, M., Ramakrishna, S., "A review on polymer nanofibers by electrospinning and their applications in nanocomposites," Composites Science and Technology 63 (2003), p. 2223-2253.

Kwoun, S.J., Lee, R.M., "A Novel Polymer Nanofiber Interface for Chemical Sensor Applications," 2000 IEEE/EIA International Frequency Control Symposium and Exhibition, p. 52-57.

Lee, S-H., Ku, B-C, Wang, X., Samuelson, L.A., Kumar, J., "Design, Synthesis and Electrospinning of a Novel Fluorescent Polymer for Optical Sensor Applications," Mat. Res. Soc. Symp. Proc. vol. 708 (2002), p. BB10.45.1-BB10.45.6.

Li, Dan and Xia, Younan, "Electrospinning of Nanofibers: Reinventing the Wheel?" Adv. Mater. 2004, 16, No. 14, Wiley-VCH Verlag GmbH & Co., Weinheim, Germany.

Zong, X., Kim, K., Fang, D., Ran, S., Sxiao, B.S., Chu, B., "Structure and process relationship of electrospun bioabsorbable nanofiber membranes," Polymer 43 (2002), p. 4403-4412.

*Primary Examiner* — In Suk Bullock
*Assistant Examiner* — Dennis M White
(74) *Attorney, Agent, or Firm* — Bose McKinney & Evans LLP

(57) ABSTRACT

The invention concerns test elements, in particular diagnostic test elements, for determining the presence or concentration of biological, medical or biologically or medically effective substances including nucleic acids, proteins, viruses, microorganisms and cells, characterized in that these test elements contain nanofibers.

32 Claims, No Drawings

TEST ELEMENT WITH NANOFIBERS

RELATED APPLICATIONS

This is a continuation of U.S. patent application Ser. No. 12/880,441 filed on Sep. 13, 2010, which is a divisional of U.S. application Ser. No. 11/759,268 filed on Jun. 7, 2007 (now U.S. Pat. No. 7,815,855), which is a continuation of International Application PCT/EP2005/013066, filed Dec. 6, 2005, which claims priority to DE 10 2004 058 924.0, filed Dec. 7, 2004, all of which are each hereby incorporated herein by reference in their entirety.

BACKGROUND

The invention concerns test elements, in particular diagnostic test elements, for determining the presence or concentration of biological, medical or biologically or medically effective substances including nucleic acids, proteins, viruses, microorganisms and cells, characterized in that these test elements contain nanofibers.

Diagnostic test elements, and in particular, test strips, contain a wide variety of fiber-based materials. Papers or fleeces are especially noteworthy. Fleeces in particular are used to separate undesired sample components. As an example, reference is made to blood separation fleeces in glucose tests or in the test strips from, e.g., the Reflotron® system. The fibers that are used in papers or fleeces of the prior art are characterized by diameters between about 5 µm and 200 µm.

Nanofibers have been basically known since about 1930. They are produced by the so-called electrospinning process in which a thin fiber is produced by applying a high voltage in the range of 10-55 kV to a droplet of a polymer solution or polymer melt (Formhals, A., U.S. Pat. Nos. 1,975,504; 2,160, 962; 2,187,306).

Nanofibers have extremely small diameters. Fibers having diameters of 10-2000 nm are obtainable depending on the material. In some cases branched fibers are obtained or fibers are obtained which contain a variable number of polymer beads which can be of different sizes on the fibers. Important influencing variables are known to a person skilled in the art or may be found in the pertinent literature (e.g., Li and Xia, Adv. Matter. 16 (2004), 1151-1170).

The use of nanofibers in medical products is described in U.S. Publication No. 2003/0171053. This publication concerns a medical device which is covered with a nanofiber layer in order to improve biocompatibility. Other publications relate to a brain probe which is coated with nanofibers to improve the biocompatibility and measuring stability (e.g., U.S. Publication No. 2002/0106496 or DiPaolo et al., Proc. $2^{nd}$ Joint EMBS/BMES Conf. Houston Tex., USA, 23-23, October 2002).

U.S. Publication No. 2003/0217928 discloses a process for the electrosynthesis of nanostructures which can be used to detect an analyte also within an electrically conductive array.

WO 02/40242 describes a process for producing products for medical and cell-biological use, e.g., stents by electrospinning nanofibers based on collagen.

WO 03/026532 describes the use of nanofibers for medical devices, for example, balloons, catheters, filters and stents.

WO 03/087443 discloses a process for applying nanofibers to an object, for example medical devices such as stents, or devices for the controlled release of drugs.

Feng et al. (Angew. Chem. Int. Ed. 42 (2003), 800-802) and Feng et al. (Angew. Chem. Int. Ed. 41 (2002), 1221-1223) describe the production of "superhydrophobic" surfaces made of short nanofibers.

The use of fibers of the usual diameter in test elements for diagnostic applications has specific disadvantages, especially relating to the separation of blood cells. The fiber matrices in known test elements typically have relatively coarse, non-uniform porosity. Blood cells are either not retained by the large pores or they are retained in the interior of a fabric layer or fleece. The large pores cause lysis due to the high capillarity or due to injury or rupture of the membrane of red blood corpuscles on sharp corners and edges, especially in the case of glass fiber fleeces. Another disadvantage of fleeces or fabrics of the prior art is that these materials become relatively thick and retain correspondingly large volumes of liquid in the interstitial space of the fibers. This is problematic in the context of the development trend towards smaller and smaller sample volumes.

Structures made of hydrophobic conventional fibers can be used as liquid barriers. Examples of these are known under the trade name Tyvek®. However, a disadvantage of these structures is that an aqueous solution which comes into contact with these fabrics rolls off the surface, which is why they are not able to penetrate into the pores.

SUMMARY AND DESCRIPTION

The present invention provides test elements for detecting an analyte which at least partially eliminate the disadvantages of the prior art. More particularly, the invention relates to the use of nanofibers for the production of test elements, e.g., test strips, arrays or sensors. Nanofibers in the sense of the present invention include electrospun and/or continuous fibers. The fibers preferably have a diameter of 10-2000 nm, particularly preferably of 10-1000 nm, and most preferably of 10-500 nm. Preferred electrospun or continuous nanofibers can be manufactured in any length. For an application in test elements, the fibers preferably at least have a length of $\geq 1$ mm, particularly preferably of $\geq 2$ mm. This is in contrast to the short nanofibers described by Feng et al. (2002), supra, and Feng et al. (2003), supra.

The nanofibers in the context of these teachings can be hydrophilic nanofibers, hydrophobic nanofibers and mixtures thereof.

The nanofibers are manufactured from polymers by an electrospinning process. Suitable processes are disclosed in the aforementioned documents of the prior art. Examples of suitable polymers are organic polymers including polyolefins such as polyethylene, polypropylene, cycloolefin polymers such as Topas®, polypentene or copolymers thereof, fluorinated or partially fluorinated polymers such as polytetra fluoroethylene or others, polyesters such as polyterephthalate, polyamides such as poly-ε-caprolactam, polyurethanes, polyaromatic compounds such as poly[p-xylylene] and derivatives thereof, polyvinyl alcohols, polyvinylamines, polyethyleneimines, polyalkylene oxides such as polyethylene oxides or combinations or copolymers thereof. Furthermore, it is also possible to use inorganic nanofibers such as nanofibers based on oxides such as silicates, e.g., glass such as silicate, alkali silicate, quartz or water glass, or nanofibers based on metal alkoxy condensates or combinations thereof. Combinations of organic and inorganic nanofibers can also be used.

The nanofibers as components of analytical test elements can be provided in the form of fleeces, fabrics, membranes, layers or combinations thereof. As mentioned above, such materials can be produced by electrospinning polymers from solution or from a melt.

Such a nanofiber material can be produced by depositing the fibers in a disordered manner. It is also possible to deposit the fibers in a more or less ordered manner in order to achieve isotropic or anisotropic effects. The material properties can be influenced within wide limits by the selection of the material as well as by the selection of fiber diameter, fiber density, and spinning parameters.

Such a nanofiber material can be applied to a test element, e.g., a test strip, by simply spinning the fibers onto the surface. They can also be calendered onto the surface or applied to an adhesive layer such as an acrylate adhesive, a contact adhesive or an adhesive tape. It is also possible to partially solubilize the support material by a solvent and to deposit fibers onto the swollen material, just as it is possible to achieve a dissolving effect on the surface of the support using a suitable solvent during the production of the fibers, which then results in a permanent bond between the nanofibers and the surface after the solvent has evaporated. This occurs, for example, more easily when the conditions are selected such that nanofibers with beads are formed. It is, however, also readily possible to mix these fibers with other fibers from another nozzle or, after applying a first layer containing beads, which results in a particularly good bond with the support material, to apply an additional layer comprising fibers of a different design and thickness and/or material.

The test element which contains the nanofibers can, for example, be a test strip, an array or a sensor such as an electrochemical sensor. Nanofibers can be applied to porous or non-porous materials of the test element.

In one embodiment, the test element contains a test strip which comprises at least one porous support material, for example, in the form of a paper, a fleece and/or a membrane, and the nanofibers can be applied to at least one surface of such a porous support material.

Deposition of the nanofibers onto a conventional paper or fleece or a membrane enables the surface of this support material to be modified in such a manner that a substantially finer pore size is achieved on the coated upper side. This allows completely different and substantially improved filter properties to be achieved. Material modified in this manner can be applied in a known manner to a test strip by gluing or laminating, etc. On the other hand, the material of the test strip or individual components thereof can also be composed completely of nanofibers.

For example, nanofibers can be used in filter elements to separate particulate components from a sample. In one exemplary embodiment, the filter element is an element for separating blood cells, preferably erythrocytes.

In so doing, it is possible to eliminate the tendency for hemolysis by using nanofibers in blood separation fleeces because the fine fibers support the erythrocyte membrane and the erythrocyte membrane is not torn due to capillary activity. It is also virtually impossible for the few fine fiber ends of nanofibers to damage the membrane of erythrocytes and thus cause hemolysis. It is possible by using a fleece made of nanofibers to prepare a very thin fleece, e.g., having a thickness of 0.02 µm to 50 µm, preferably 0.05 µm to 5 µm, particularly preferably 0.08 µm to 2 µm, with a high filter effectiveness which is then also able to process very small volumes of blood and itself has only a very small retention. In this application, hydrophilic polymers can be used, such as polyamides, polyurethanes, polyvinyl alcohols, polyvinylamines, polyethyleneimines, polyethylene glycols or copolymers thereof, e.g., of polyurethane and polyethylene glycol in order to produce nanofibers therefrom by electrospinning. Equally preferred are inorganic materials such as oxides, preferably glasses such as quartz, silicate, alkali silicate, water glass, metal alkoxy condensates, or combinations thereof.

In another exemplary embodiment, nanofibers can be applied to the surface of a support material in order to modify its properties and in particular with regard to its ability to be wetted with liquids. Thus, a hydrophobic surface, e.g., a non-porous surface such as the test field of an array, can be coated with hydrophilic nanofibers to increase its wettability. A hydrophilic surface in this context preferably has an intrinsic contact angle of <90° with water.

Intrinsic contact angle denotes the contact angle on an ideally smooth surface which is used as a measure for the surface energy determined by chemical groups without any influence by the surface geometry.

For example, the wetting properties can be dramatically changed by depositing nanofibers on surfaces. Whereas a drop of water forms a contact angle of about 70-80 degrees on pure poly(methyl methacrylate) PMMA surfaces, a drop of water spreads on a PMMA surface which has been partially covered with a thin layer of nanofibers made of polyamide (PA). An amount of 10-500 mg/m$^2$, in particular of 50-300 mg/m$^2$, e.g., about 200 mg/m$^2$, nanofibers, e.g., made of poly-ε-aminocaprolactam having a thickness of 20-2000 nm, e.g., 600 nm has proven to be particularly advantageous.

On the other hand, non-porous surface such as a test strip housing, in particular in the region of the sample application zone or an area between the test fields of an array, etc., can be coated with hydrophobic nanofibers in order to reduce the wettability of the surface and to produce a surface having hydrophobic or super-hydrophobic properties. In this connection, a hydrophobic surface in the sense of the present invention preferably has an intrinsic contact angle of $\geq 90°$ with water. A superhydrophobic surface in this context preferably has a contact angle of $\geq 140°$, preferably of $\geq 150°$ with water.

A nanofiber coating as a hydrophobic barrier having superhydrophobic properties is of special interest when developing a hygienic test strip where it is absolutely essential to prevent sample liquid such as blood from remaining adhered to the test strip. In order to achieve this, a nanofiber structure is manufactured by electrospinning from a hydrophobic base material, e.g., a fluorinated or partially fluorinated polymer such as polytetrafluoroethylene (PTFE), a modified soluble PTFE such as Teflon® AF, a copolymer of tetrafluoroethylene and hexafluoropropylene (FEP), partially fluorinated polyurethanes, fluorinated polyaromatic compounds or others, or a polyolefin PP, polypentene or others, or polyolefin copolymers. Even a very thin, e.g., 2 µm, layer of such fiber materials or of fibers with beads can be used to create a super-hydrophobic surface on which a drop of water has a contact angle of $\geq 140°$. A drop of water placed on such a surface already rolls off at a slope of below 20°. A drop of blood which is brought into contact with the surface of such a layer exhibits no tendency to wet this layer or adhere to this layer.

One exemplary embodiment is a test element comprising (a) at least one area covered with hydrophilic nanofibers and (b) at least one area covered with hydrophobic nanofibers. The areas covered with hydrophilic nanofibers are preferably test fields which are provided for the application of sample liquids such as blood in order to improve their wetting. The areas covered with hydrophobic nanofibers are preferably arranged in the vicinity of the test fields and/or sample application sites in order to prevent an undesired wetting with sample liquid.

In yet another embodiment, a mixture of hydrophilic and hydrophobic nanofibers can be applied to a surface, e.g., to a non-porous surface for a more uniform distribution of liquids over the surface. Examples of fiber mixtures are Teflon® AF and poly(urethane-g-ethylene oxide).

By applying a thin layer of a mixture of hydrophilic and hydrophobic nanofibers it is possible to modify a surface in such a manner that the applied drop of liquid and in particular an aqueous drop is uniformly distributed. Surprisingly, it has been found that when such a drop dries, substances dissolved therein form a substantially more uniform layer than without the presence of nanofibers. In this manner it is possible to distribute a test chemistry applied in liquid form in a substantially more uniform manner than previously, e.g., on an electrode of an electrochemical sensor. This is also of importance for the production of arrays, e.g., that are used in molecular-diagnostic analyses. In particular, the aspect of self-fluorescence plays a major role in these applications. The extremely small amount of material, e.g., 10-500 mg/m$^2$ which is necessary for the effect results in only a very low self-fluorescence, which in turn has a favourable effect on the signal-to-noise ratio when evaluating the arrays.

These teachings also may be applied in a method for the qualitative and/or quantitative determination of an analyte in a sample in which a test element as described above is used. The method can be an immunochemical method or a method based on nucleic acid hybridization or also an enzymatic method. Applications include electrochemical and/or photometric detection methods, e.g., for detecting glucose in blood or other body fluids.

Yet a further application of these teachings is the use of nanofiber material, preferably of electrospun and/or continuous nanofibers as described above, as a filter in a test element which is used to detect analytes. The filter can contain the nanofibers as such and/or they can be applied to a porous support material as mentioned above. If the filter contains the nanofibers as such, i.e., in an unsupported form, the material is present as an optionally asymmetric membrane. As mentioned above, the material of the membrane can contain hydrophilic nanofibers, hydrophobic nanofibers or mixtures thereof.

Advantageously, fleeces or filter materials can be produced for use on test strips which are substantially thinner and have a much finer and more uniform pore size and require less material than the materials according to the state of the art. It is also advantageous that the wettability of surfaces can be dramatically improved by nanofibers. Another advantage is that superhydrophobic surfaces can be produced from hydrophobic polymers on which a drop of water or drop of blood does not hold but rather rolls off at a slight angle. It is also advantageous that virtually no hemolysis occurs when blood is separated. Nanofibers enable detection reagents to be applied to surfaces in a substantially more homogenous manner than was previously the case and the self-fluorescence can be reduced.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A test element for detecting an analyte in a bodily fluid sample, comprising an electrochemical or photometric detection reagent for detecting the analyte in the bodily fluid sample, the detection reagent and nanofibers applied to a porous or non-porous support material, at least some of the nanofibers containing more than one polymer bead thereon and having a length of at least 2 mm.

2. The test element of claim 1, further comprising continuous nanofibers.

3. The test element of claim 1, wherein the nanofibers are obtained by electrospinning.

4. The test element of claim 1, wherein the nanofibers have a diameter of 10 to 2000 nm.

5. The test element of claim 1, wherein the nanofibers have a diameter of 10 to 1000 nm.

6. The test element of claim 1, wherein the nanofibers have a diameter of 10 to 500 nm.

7. The test element of claim 1, wherein the nanofibers comprise hydrophilic nanofibers, hydrophobic nanofibers or mixtures thereof.

8. The test element of claim 7, wherein the hydrophobic nanofibers form a surface of the test element having superhydrophobic properties.

9. The test element of claim 1, wherein the nanofibers are composed of polymers selected from polyolefins, polyaromatic compounds, fluorinated or partially fluorinated polymers, polyesters, polyamides, polyurethanes, polyvinyl alcohols, polyvinyl amines, polyethyleneimines, polyalkylene oxides and combinations and copolymers thereof.

10. The test element of claim 1, wherein the nanofibers comprise fleeces, fabrics, membranes, layers or combinations thereof.

11. The test element of claim 1, wherein the test element comprises a test strip.

12. The test element of claim 1, wherein the test element comprises a test array.

13. The test element of claim 1, wherein the nanofibers are applied to a porous support material selected from papers, fleeces and membranes.

14. The test element of claim 13, wherein the nanofibers are applied to at least one surface of the porous support material.

15. The test element of claim 13, wherein the nanofibers comprise a filter element for separating particulate components from a sample.

16. The test element of claim 15, wherein the filter element is configured for separating blood cells from a blood sample.

17. Test element according to claim 1, wherein the nanofibers are applied to the surface of a non-porous support material.

18. The test element of claim 1, further comprising a surface coated with hydrophilic nanofibers to increase the wettability of the surface.

19. The test element of claim 1, wherein the porous or non-porous support material comprises a surface coated with hydrophobic nanofibers to reduce the wettability of the surface.

20. The test element of claim 19, wherein the coated surface has superhydrophobic properties.

21. The test element of claim 1, further comprising at least one first area covered with hydrophilic nanofibers and at least one second area covered with hydrophobic nanofibers.

22. The test element of claim 1, further comprising a surface coated with a mixture of hydrophilic and hydrophobic nanofibers, the surface being configured for uniform distribution of liquids applied thereto.

23. The test element of claim 1, wherein the nanofibers comprise a filter configured to separate red blood cells from blood in a blood sample.

24. The test element of claim 23, wherein the filter comprises a fleece.

25. The test element of claim 24, wherein the fleece has a thickness of 0.02 µm to 50 µm.

26. The test element of claim 24, wherein the fleece has a thickness of 0.08 μm to 2 μm.

27. The test element of claim 23, wherein the nanofibers are hydrophilic.

28. The test element of claim 1, wherein the support material is hydrophobic and the nanofibers are hydrophilic.

29. The test element of claim 1, wherein the nanofibers comprise a thin layer having a mass per unit area of 10 to 50 mg/m$^2$.

30. The test element of claim 1, wherein the nanofibers comprise an asymmetric membrane.

31. The test element of claim 1 wherein the nanofibers comprise a thin layer having a thickness of 20 to 2000 nm.

32. The test element of claim 1, wherein the nanofibers comprise a hydrophobic barrier.

* * * * *